(12) United States Patent
Shibata et al.

(10) Patent No.: US 8,740,017 B2
(45) Date of Patent: Jun. 3, 2014

(54) DISPENSER FOR BOTH FOAM AND LIQUID

(75) Inventors: Miduho Shibata, Aichi (JP); Tomio Nagao, Gifu (JP)

(73) Assignee: Menicon Nect Co., Ltd., Aichi (JP)

( * ) Notice: Subject to any disclaimer, the term of this patent is extended or adjusted under 35 U.S.C. 154(b) by 0 days.

(21) Appl. No.: 13/807,826

(22) PCT Filed: Jun. 22, 2011

(86) PCT No.: PCT/JP2011/064222
§ 371 (c)(1),
(2), (4) Date: Dec. 31, 2012

(87) PCT Pub. No.: WO2012/002204
PCT Pub. Date: Jan. 5, 2012

(65) Prior Publication Data
US 2013/0104939 A1  May 2, 2013

(30) Foreign Application Priority Data
Jul. 1, 2010 (JP) .................................. 2010-151483

(51) Int. Cl.
*B65D 47/06* (2006.01)
(52) U.S. Cl.
USPC .......................... 222/190; 222/211; 222/481
(58) Field of Classification Search
USPC ................. 222/190, 189.08, 135, 136, 144.5, 222/145.5, 145.6, 145.1, 481, 481.5, 482, 222/211, 1; 134/25.1
See application file for complete search history.

(56) References Cited

U.S. PATENT DOCUMENTS

| | | | | |
|---|---|---|---|---|
| 3,850,346 A | * | 11/1974 | Richardson et al. | 222/145.7 |
| 5,174,475 A | * | 12/1992 | Day et al. | 222/144.5 |
| 5,730,322 A | * | 3/1998 | Iba et al. | 222/42 |
| 6,164,495 A | * | 12/2000 | Manesis | 222/129 |
| 7,090,097 B1 | * | 8/2006 | Kazarian et al. | 222/144.5 |
| 8,104,650 B2 | * | 1/2012 | Lang et al. | 222/571 |

(Continued)

FOREIGN PATENT DOCUMENTS

| | | |
|---|---|---|
| JP | 60-163249 U | 10/1985 |
| JP | 61-90752 U | 6/1986 |

(Continued)

OTHER PUBLICATIONS

International Search Report dated Sep. 13, 2011, as issued in corresponding International Application No. PCT/JP2010/062682, filed Jun. 22, 2011.

(Continued)

*Primary Examiner* — Paul R Durand
*Assistant Examiner* — Donnell Long
(74) *Attorney, Agent, or Firm* — Maier & Maier, PLLC (57) ABSTRACT

A dispenser used when attached to an opening of a squeeze bottle discharge a content liquid when inverted. The dispenser has a first channel to discharge a straight forward-moving liquid and a second channel to discharge a foaming liquid. The first channel has a first through channel connecting a first inlet for the content liquid to a first outlet. The second channel has a conduit that has an opening at an inner bottom of the bottle, extends to a foaming chamber, serves as an air supply channel, and has an inner diameter; the foaming chamber is connected to the conduit and mixes the content liquid with air to foam the content liquid; and a second through channel connecting the foaming chamber to a second outlet.

7 Claims, 8 Drawing Sheets

(56) References Cited

U.S. PATENT DOCUMENTS

| | | | |
|---|---|---|---|
| 8,365,965 B2 * | 2/2013 | Ophardt | 222/321.8 |
| 8,376,190 B2 * | 2/2013 | Choi et al. | 222/190 |
| 2002/0153389 A1 * | 10/2002 | Creaghan et al. | 222/190 |
| 2011/0272432 A1 * | 11/2011 | Baughman | 222/136 |

FOREIGN PATENT DOCUMENTS

| | | | | |
|---|---|---|---|---|
| JP | 61090752 U | * | 6/1986 | B65D 47/26 |
| JP | 02-102366 U | | 8/1990 | |
| JP | 03/503380 A | | 8/1991 | |
| JP | 08-252508 A | | 10/1996 | |
| JP | 11-114461 A | | 4/1999 | |
| JP | 2000-246154 A | | 9/2000 | |
| JP | 2008-155986 A | | 7/2008 | |
| WO | 89/09655 A1 | | 10/1989 | |

OTHER PUBLICATIONS

Daisuke Saito, "Former Yoki no Tokucho to Saikin no Gijutsu Doko", Fragrance Journal, Jul. 15, 2006, pp. 54 to 59, vol. 34, No. 7.

* cited by examiner

DISPENSER FOR BOTH FOAM AND LIQUID

RELATED APPLICATIONS

This application is the U.S. national stage application which claims priority under 35 U.S.C. §371 to International Patent Application No.: PCT/JP2011/064222, filed on Jun. 22, 2011, which claims priority under 35 U.S.C. §119, to Japanese Patent Application No.: 2011-151483, flied Jul. 1, 2010, the disclosures of which are incorporated by reference herein their entireties.

TECHNICAL FIELD

The present invention relates to a dispenser that is to be attached to an opening of a squeeze bottle configured to discharge a content liquid when inverted and that can discharge each of a straight forward-moving liquid and a foaming liquid. The invention also relates to a dispenser that can selectively discharge a straight forward-moving liquid or a foaming liquid. The invention also relates to a method for using the dispenser to clean and store contact lenses.

BACKGROUND ART

Solutions including a surfactant, such as hand soaps, body washes, shampoos, dishwashing liquids, and contact lens cleaning solutions, are being distributed in the market as contained in a predetermined container. Such a solution is typically foamed due to effects of the surfactant contained therein. The foaming solution envelopes an object to be cleaned and removes oil stains from the object without damaging the object. Specifically, the solution is in foam form when used for cleaning, while it is in liquid form when distributed or used for storage. Considering ease of use, there have been made some proposals on a container that allow a liquid to be supplied in foam form from an outlet of a container.

Discharging a solution in a container requires making the internal pressure higher than atmospheric pressure. For example, there are known so-called aerosol containers, where a gas for pressure increase is previously encapsulated. However, aerosol containers are sometimes questioned in terms of environmental problems, effective use of resources, or the like, since CFCs, propane, or the like are used as a gas for pressure increase. Further, there are many problems when the user reuses an aerosol container that the user has used on hand. On the other hand, there have been made proposals for increasing the internal pressure of a container using a manual pump, piston, or the like, including the following: (1) A proposal on a trigger sprayer where the cap of a nozzle assembly rotates around three positions: stop, spray, and foam (Patent Document 1); (2) A proposal on a nozzle which can select among continuous flow, mist, and foam in a trigger sprayer where a spray pump is attached to an opening of a bottle-shaped container and that sucks up a content liquid to a liquid chamber by depressing and releasing the spout of the spray pump during use and sprays the content liquid out of the spray outlet of the spout (Patent Document 2); (3) A proposal on a discharge mode selection device of a trigger pump dispenser which can select among all discharge modes: straight forward-flow, swirling, and foam, and causes no disturbance to each discharge flow (Patent Document 3); and (4) A proposal on a trigger liquid discharge device which allows the user to easily position a nozzle cap by means of a touch of a finger tip, a color or pattern based on vision, or the like in selecting the desired spray state of a spray nozzle (Patent Document 4).

These trigger sprayer devices have ease of use and are preferable to aerosol containers in terms of environment problems. However, trigger nozzles have problems to be solved in terms of the structural complexity thereof. Further, trigger nozzles can raise the proportion of the cost of the container or the like in the total price, although the solution is the purpose of the sale.

In view of the foregoing, as the most simple means for increasing the internal pressure of a container, there are so-called squeeze bottles, which discharge a content liquid by grasping the container and thus deforming it. Methods for selectively discharging foam or liquid from such a squeeze container include the following proposals: a proposal on a nozzle for both foam and liquid where a foam spray outlet communicating with the interior of a container body, and a liquid spray outlet are formed separately and where an outer lid for closing the foam spray outlet and the liquid spray outlet is rotatably inserted into an inner lid (Patent Document 5); and a proposal on a switching valve configured so that a liquid can flow from upstream to downstream when the container is uptight and cannot flow from upstream to downstream when the container is inverted (Patent Document 6). The above-mentioned proposals are common in that a ball-shaped valve is present on a channel for a liquid and that a liquid is selectively sprayed when the container is uptight or inverted. Further, the proposals have a simpler structure than trigger containers. Furthermore, since which of foam and liquid is to be discharged is determined based on whether the container is uptight or inverted, the proposals have an advantage in that selection of foam or liquid is clear. However, the user is required to handle the container in different orientations or in different ways. Accordingly, the feeling of use can be impaired. What is particularly inconvenient is that in the handling of small contact lenses, it is difficult to place foam discharged from the uptight container onto the lenses correctly.

A study on such containers for a foaming liquid, "Features of Foamer Containers and Recent Technical Trend" (Non-Patent Document 1) states "As consumers raise awareness of safety and resource saving, non-gas type foamer containers (referring to trigger bottles or squeeze bottles) have ease of use and can be said to be containers matching these days. Large products have been commercialized in the fields of hand soap and the like. The name recognition of foamer containers is being increased among consumers. To further increase foamer containers, I believe that it is necessary to repeatedly improve foamer containers in accordance with consumer needs." It is important to propose new foamer containers in accordance with the diversification of consumer needs in the market.

PRIOR ART DOCUMENTS

Patent Documents

Patent Document 1: Japanese Unexamined Patent Application Publication (translation of PCT application) No. 3-503380

Patent Document 2: Japanese Unexamined Patent Application Publication No. 11-114461

Patent Document 3: Japanese Unexamined Patent Application Publication No. 8-252508

Patent Document 4: Japanese Unexamined Patent Application Publication No. 2000-246154

Patent Document 5: Japanese Unexamined Utility Model Registration Application Publication No. 2-102366

Patent Document 6: Japanese Unexamined Patent Application Publication No. 2008-455986

Non-Patent Documents

Non-Patent Document 1: *FRAGRANCE JOURNAL, No. 7*, pp. 54 to 59, 2006,

SUMMARY OP THE INVENTION

Problems to be Solved by the Invention

As described above, an object of the present invention is to provide a dispenser that is to be attached to an opening of a squeeze bottle and that can spray each of a foaming liquid and a straight forward-moving liquid in accordance with the application with the squeeze bottle inverted, as well as is environmentally friendly and low-cost and has a simple structure. Further, a specific method for using this dispenser is proposed.

Means for Solving the Problems

To solve the problems and accomplish the object, a dispenser according to the present invention is characterized in that the dispenser is to be attached to an opening of a squeeze bottle and is provided with a first channel configured to discharge a straight forward-moving liquid and having a configuration described below and a second channel configured to discharge a foaming liquid and having a configuration described below. The first channel has a first through channel connecting a first inlet for a content liquid to a first outlet. The second channel has a conduit that has an opening at an inner bottom of the bottle, extends to a foaming chamber, serves as an air supply channel, and has an inner diameter of 0.8 to 4 mm; the foaming chamber connected to the conduit and configured to mix the content liquid with air to foam the content liquid; and a second through channel connecting the foaming chamber to a second outlet. A second inlet for the content liquid leading to the conduit is for and with an inner diameter size of 0.06 to 2 mm at a portion adjacent to the foaming chamber.

A straight forward-moving liquid refers to a liquid whose foam portion takes an about 30% or less of the total volume when poured into, for example, another container after supplied from the outlet. It does not necessarily refer to a liquid containing no foam. Straight forward-moving liquids include liquids which move straight forward from the outlet, as well as liquids which are discharged obliquely at an appropriate angle. On the other hand, a foaming liquid refers to a liquid whose foam portion takes about 70% or more of the total volume and does not necessarily refer to a liquid whose foam portion takes 100% of the total volume.

The first channel is formed as a through channel having no obstacle, so as to supply the content liquid in non-foam form. On the other hand, the second channel has, as an air inlet, a conduit having a length reaching the internal bottom of the bottle, so as to mix the liquid with air to foam the liquid. The present invention is a dispenser to be attached to a squeeze bottle, and the bottle is inverted in order to discharge the content liquid. At this time, air is gathered at the bottom of the bottle. The conduit is formed in order to supply air to the foaming chamber. Further, to supply the content liquid to the foaming chamber simultaneously, the second inlet for the content liquid is formed in front of the foaming chamber.

The respective outlets of the first and second channels are provided with caps for closing the outlets. Thus, a straight forward-moving liquid or foaming liquid can be selectively used in accordance with the intent of the user. Alternatively, a system may be employed so as to discharge a selective liquid on the basis of the open or close of each channel rather than on the basis of the presence or absence of the cap. In the configuration of such a dispenser, a hollow support member having the first and second channels formed separately therein and a rotational member rotatably supported in the hollow of the support member are preferably provided, and at least part of the first through channel and the foaming chamber are preferably provided in the rotational member separately. In the dispenser having thus configured, when the first through channel communicates with the first outlet (that is, the first channel opens to traffic) by rotating the rotational member by a predetermined angle, the foaming chamber is isolated from one of the conduit and the second through channel (that is, the second channel is closed). On the other hand, when the conduit, the foaming chamber, and the second through channel communicate with one another (that is, the second channel opens to traffic) by rotating the rotational member by a predetermined angle, the first through channel is closed (that is, the first channel is closed). Owing to this structure, time and effort to open or close the caps each time are omitted in continuously using the straight forward-moving liquid and the foaming liquid. That is, high user convenience is provided.

Alternatively, an outlet may be shared in selectively discharging a liquid. Such a dispenser is characterized in that if part of the first through channel formed in the rotational member is defined as a third through channel, the first through channel includes the second through channel and the third through channel and that the second through channel is shared by the second channel and the first channel. The shared use of the second through channel leading to the outlet by the first and second channels allows the structure of the dispenser to be further simplified.

A ratio of an inner diameter of the second inlet to an inner diameter of the conduit at the position where the air and the content liquid are merged is preferably 1/50 to 40/50. Thus, the air and the content liquid can be efficiently mixed, forming soft and smooth foam. The inner diameter of a portion of the conduit immediately before communicating with the second inlet is preferably reduced to about 1/5 to 4/5 so that the liquid from the second inlet easily involves air.

In the present invention, the foaming chamber preferably has a configuration where it is a hollow tube having openings on a side thereof adjacent to an outlet and a side thereof adjacent to an inlet and where the openings of the hollow tube are covered by screen filters, respectively. A mesh of the screen filter adjacent to the inlet is set as being coarser than a mesh of the screen filter adjacent to the outlet. Such a structure allows the foaming effect to be further increased.

Further, contact lenses can be cleaned using the foaming liquid discharged from the dispenser having the above-mentioned structure, as well as can be stored in a contact lens container filled with the straight forward-moving liquid.

Effect of the Invention

The dispenser according to the present invention has a simple structure and therefore can be manufactured at low cost without requiring any special equipment. Further, the dispenser according to the present invention can spray each of a foaming liquid and a straight forward-moving liquid in accordance with the application when the dispenser is attached to an opening of a squeeze bottle. After exhausting the content liquid in the bottle, the dispenser can be used repeatedly by detaching the dispenser and replenishing the bottle with the content liquid, or attaching the dispenser to another bottle. Accordingly, it is possible to provide an environmentally friendly dispenser.

In particular, this dispenser is suitable for an application where the same solution is assumed to be used in two states, a foaming state and a straight forward-moving state. Specifically, it is possible to propose a care method having ease of use by using the dispenser to clean and store contact lenses.

EMBODIMENTS FOR CARRYING OUT THE INVENTION

Hereafter, a dispenser according to the present invention will be described in detail with reference to the drawings.

Figure 1:
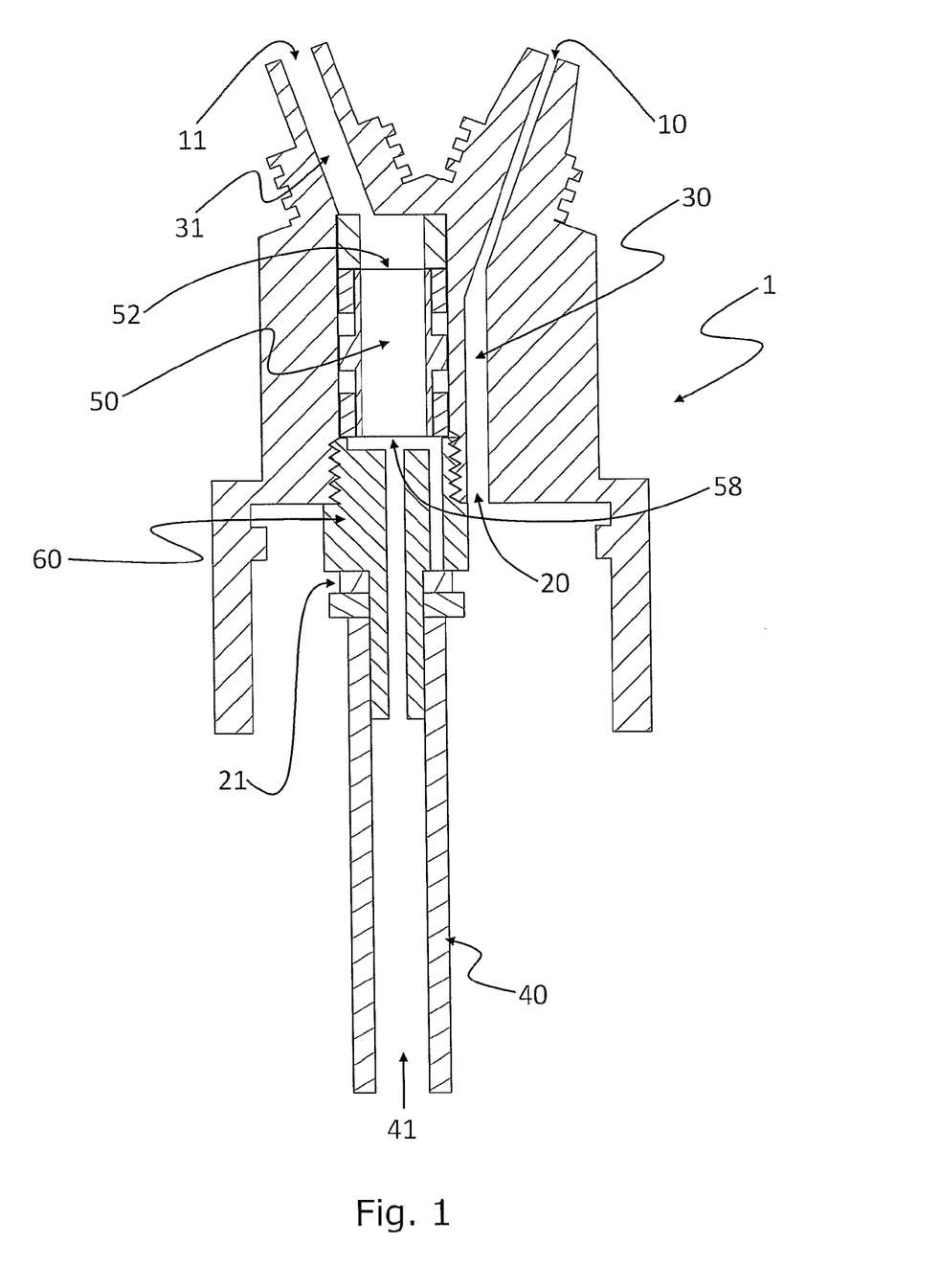
FIG. 1 is a drawing showing an aspect of a dispenser according to the present invention as a sectional view.
Figure 2:
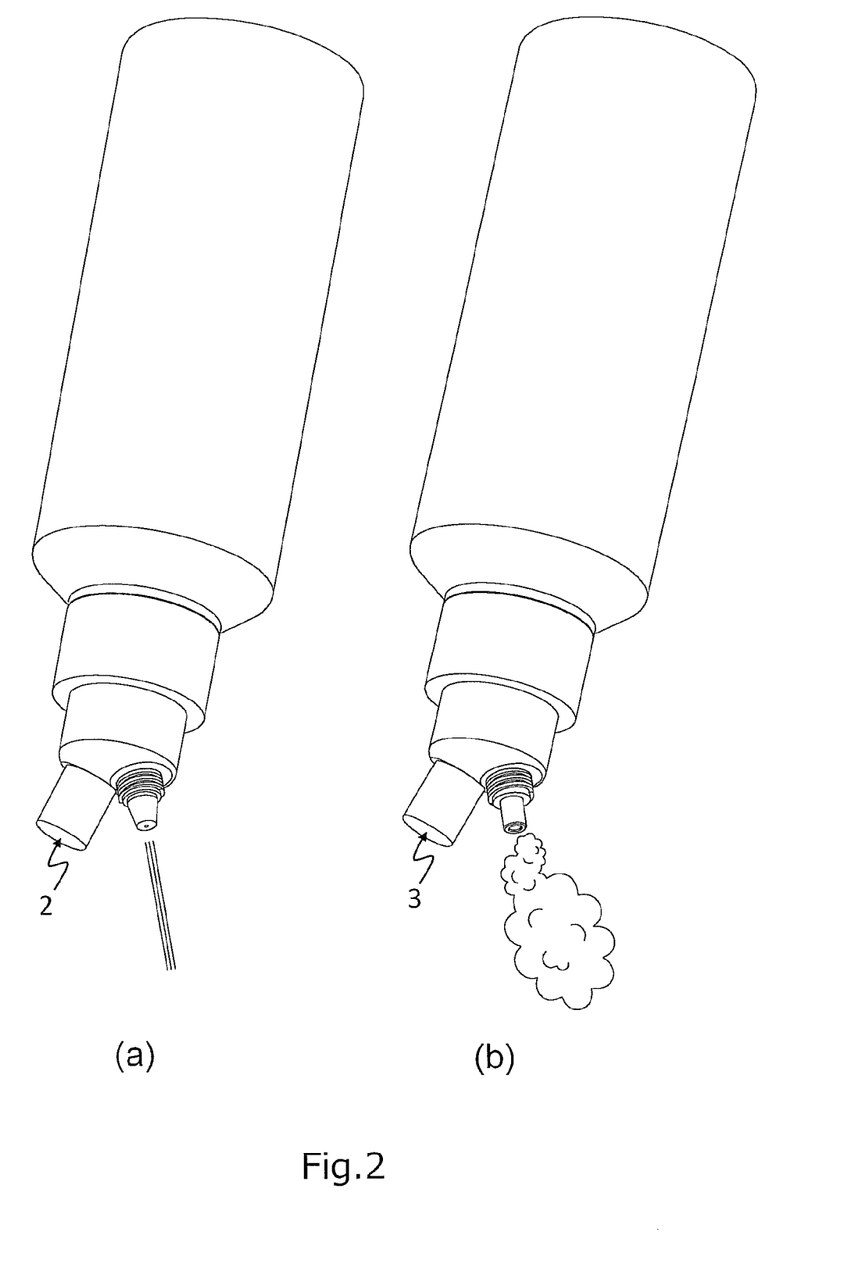
FIG. 2 is a drawing showing the discharge of (a) a straight forward-moving liquid and (b) a foaming liquid.

FIG. 1 schematically shows a longitudinal section of an embodiment of a dispenser 1 according to the present invention. A first outlet 10 is formed in an upper-right portion of the drawing, and a second outlet 11 is formed in an upper-left portion thereof. A first inlet 20 for a content liquid communicates with the first outlet 10, and a first through channel 30 extends from the first inlet 20 to the first outlet 10. In this example, a first channel for discharging a straight forward-moving liquid includes the first inlet, the first through channel, and the first outlet. It is understood that by compressing the bottle by fingers, the content liquid is discharged from the bottle via the channel without any problem (see FIG. 2(a)). While the first through channel is shown in FIG. 1 as being bent in a doglegged shape, it may extend from the first inlet 20 toward the first outlet 10 in a straight line. A horizontal sectional shape of the first through channel need not necessarily be circular or oval and may be polygonal. While the inner diameter of the first through channel is 0.5 to 2.0 mm, it may be constant across the total length, may be the largest at the first inlet 20 and smaller at positions closer to the outlet 10, or may be the opposite. When the inner diameter is smaller at positions closer to the outlet 10, the content liquid can be discharged vigorously. Thus, in pouring the liquid into another container, it is easy to aim the liquid at the target.

Shown in a lower-left portion of the drawing is a conduit 40 that has a length reaching the inner bottom of the bottle and an air supply inlet 41 and reaches a foaming chamber 50. Formed at a portion adjacent to the foaming chamber 50 is a second inlet 21 thr the content liquid. While the conduit 40 and the foaming chamber 50 are connected together with a connecting pipe 60 therebetween in FIG. 1, the conduit and the foaming chamber may be connected together without the connecting pipe therebetween. While the second inlet 21 is formed in the connecting pipe 60, it may be formed in the conduit. In any case, it is necessary to employ a structure which feeds both air and the content liquid into the foaming chamber. The second inlet is preferably formed at a portion adjacent to the foaming chamber (more specifically, as being separated from the foaming chamber by 0.4 to 2.0 mm) so that a foaming liquid is discharged even when the content liquid is reduced in amount.

The inner diameter of the conduit is typically designed so as to be 0.8 to 4 mm as appropriate. If the conduit has a diameter exceeding this range, a liquid retained in the conduit may be initially discharged as it is when compressing the bottle to discharge a foaming liquid. In this case, the discharged liquid may not be foaming properly. In contrast, if the conduit has a diameter falling below the range, the conduit can be clogged with components of the content liquid which have dried at some point in the conduit. As with the first through channel, the conduit need not necessarily have the same horizontal sectional shape or inner diameter across the total length thereof. Further, the conduit preferably has a proper degree of shape retainability which prevents the conduit from being easily bent by self weight. The reason is that the opening of the conduit serving as the air supply inlet is required to be located at the inner bottom of the squeeze bottle which is inverted. The conduit is formed of a material such as polyethylene, polypropylene, silicon, nylon, polystyrene, or polyvinyl chloride, preferably polyethylene, polypropylene, or silicon. The air supply inlet 41 preferably has an obliquely cut shape or has recesses or projections formed at the opening end thereof so as to prevent the air supply inlet from closely contacting the inner bottom of the bottle and thus causing complete blockage of the opening.

Figure 3:
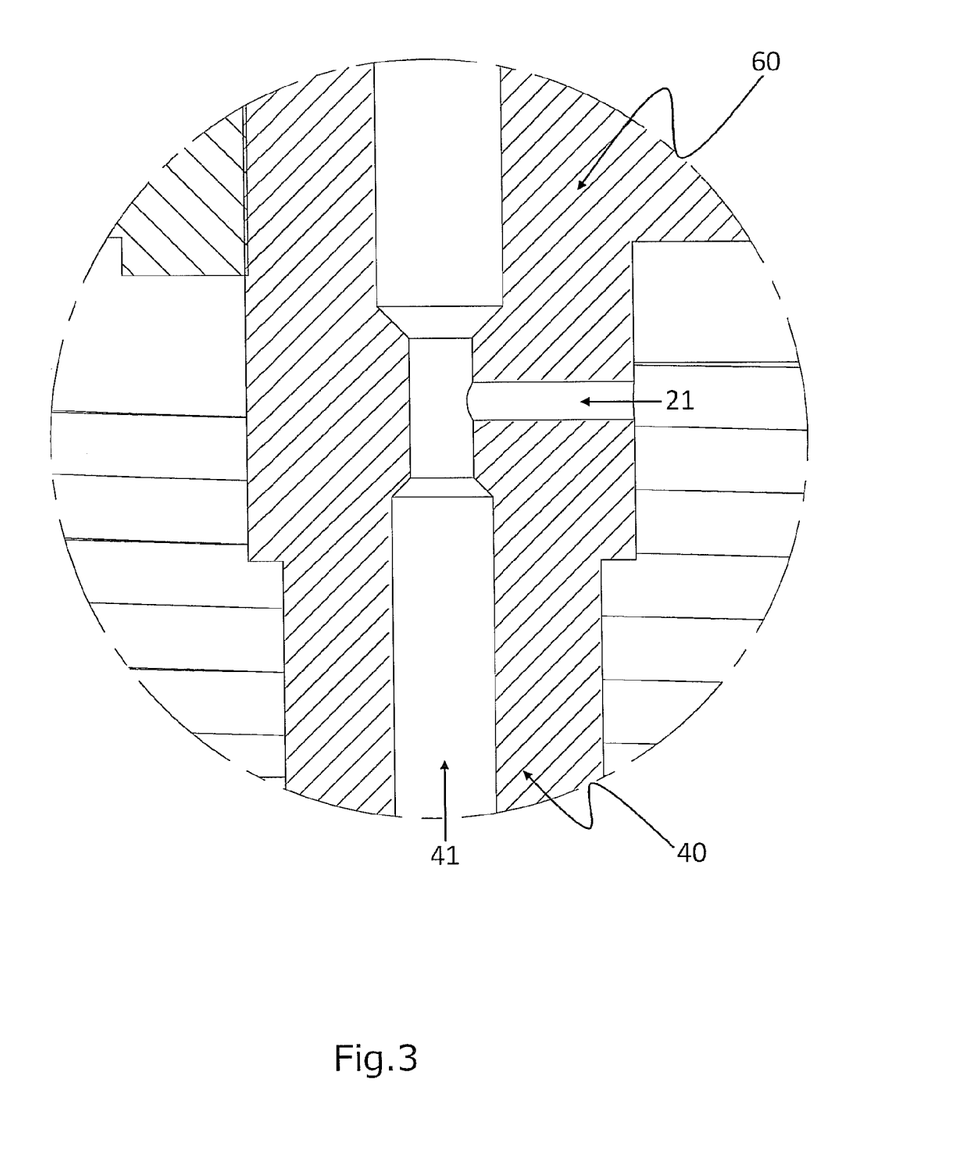
FIG. 3 is a sectional view showing a portion where air and a content liquid are merged.

The second inlet is formed with an inner diameter size of 0.06 to 2 mm. The mixture ratio between air and the liquid is susceptible to the ratio between the respective inner diameters of the second inlet and the conduit. Accordingly, obtaining the desired foaming state requires properly adjusting the ratio between the respective inner diameters of the second inlet and the conduit. Specifically, the ratio of the inner diameter of the second inlet to the inner diameter of the conduit at the position where air and the content liquid are merged is preferably 1/50 to 40/50, more preferably 1/20 to 2/3, most preferably 1/10 to 5/10. The reason is as follows: when the inner diameter of the conduit is smaller than the ratio, air is supplied insufficiently, when the inner diameter of the conduit is greater than the ratio, air is supplied excessively, and in any case, it is difficult to foam the liquid properly. As is understood from FIG. 1, the liquid that has entered the connecting pipe 60 from the second inlet 21 moves in parallel with airflow temporarily and is then mixed with the airflow immediately in front of the foaming chamber as merged with the airflow perpendicularly. The merging method is not necessarily limited to what is shown and may be a method of causing the content liquid to mix with air perpendicularly immediately after the liquid enters the connecting pipe (see FIG. 3) or a method of causing the content liquid to merge with airflow at a predetermined angle.

In FIG. 1, the conduit 40 is connected to the foaming chamber 50 with the connecting pipe 60 therebetween. The foaming chamber 50 is shown as a hollow where mesh filters are provided on as side 58 from which the content liquid and air are introduced (hereafter referred to as the inlet side) and a side 52 from which a foaming liquid is discharged (hereafter referred to as the outlet side). The foaming means is not limited to what is shown. For example, a sponge or the like having a through hole, or hollow fiber may be disposed in the foaming chamber. Although the meshes of the mesh filters are not shorn in FIG. 1, the mesh on the inlet side is preferably coarser than the mesh on the outlet side. More specifically, it is preferred to use a 100 to 300 mesh filter having an opening of 200 to 40 μm on the outlet side and a 75 to 250 mesh filter having an opening of 300 to 50 μm on the inlet side.

Figure 4:
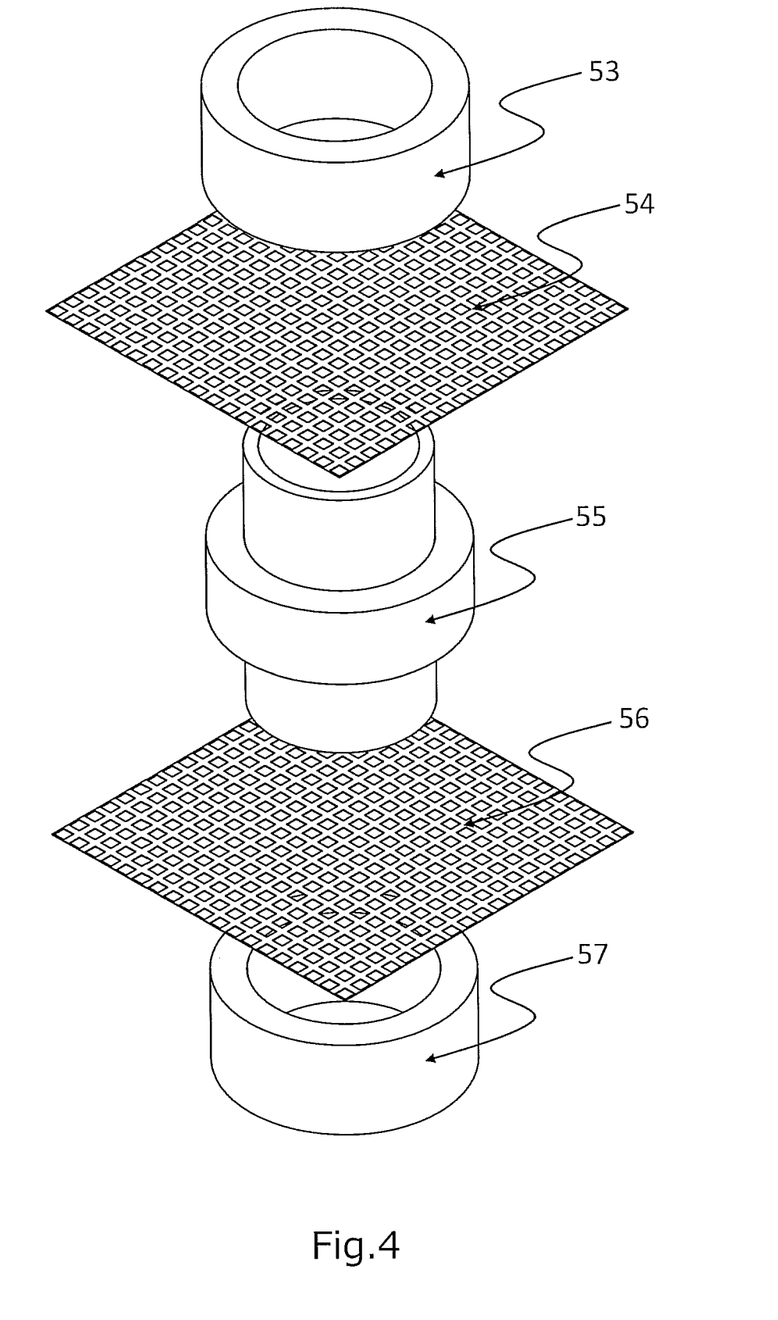
FIG. 4 is an exploded view showing an example of a foaming chamber.

The foaming chamber 50 shown in FIG. 1 more specifically has a structure as shown in FIG. 4. In FIG. 4, an annular ring 53 on the outlet side 52, a mesh filter 54 of 200 mesh having an opening of 82 μm, a tubular foaming chamber body 55 having top and bottom diameters to be inserted into annular rings, a mesh filter 56 of 100 mesh having an opening of 183 μm, and an annular ring 57 on the inlet side 58 are sequentially inserted from above. Thus, the foaming chamber 50 having a hollow whose top and bottom are covered by the mesh filters is formed. The mesh filters are formed of a material such as polyester, nylon, polypropylene, polyethylene, or Teflon®, preferably polyester or nylon.

Formed over the foaming chamber 50 is a second through channel 31 which communicates with the second outlet 11. Since the second through channel 31 has a greater diameter than the first through channel 30, a foaming liquid discharged from the foaming chamber 50 smoothly passes through the second through channel 31. The inner diameter of this through channel is about 1.5 to 4.5 mm.

In the example shown in FIG. 1, a second channel includes the conduit 40, the connecting pipe 60 having the second inlet 21, the foaming chamber 50, the second through channel 31, and the second outlet 11. It is understood that a foaming liquid (see FIG. 2(b)) can be discharged therethrough. As shown in FIG. 2, a straight forward-moving liquid or foaming liquid can be selectively used in accordance with the purpose by attaching or detaching caps 2, 3 for blocking the outlets.

Figure 5:
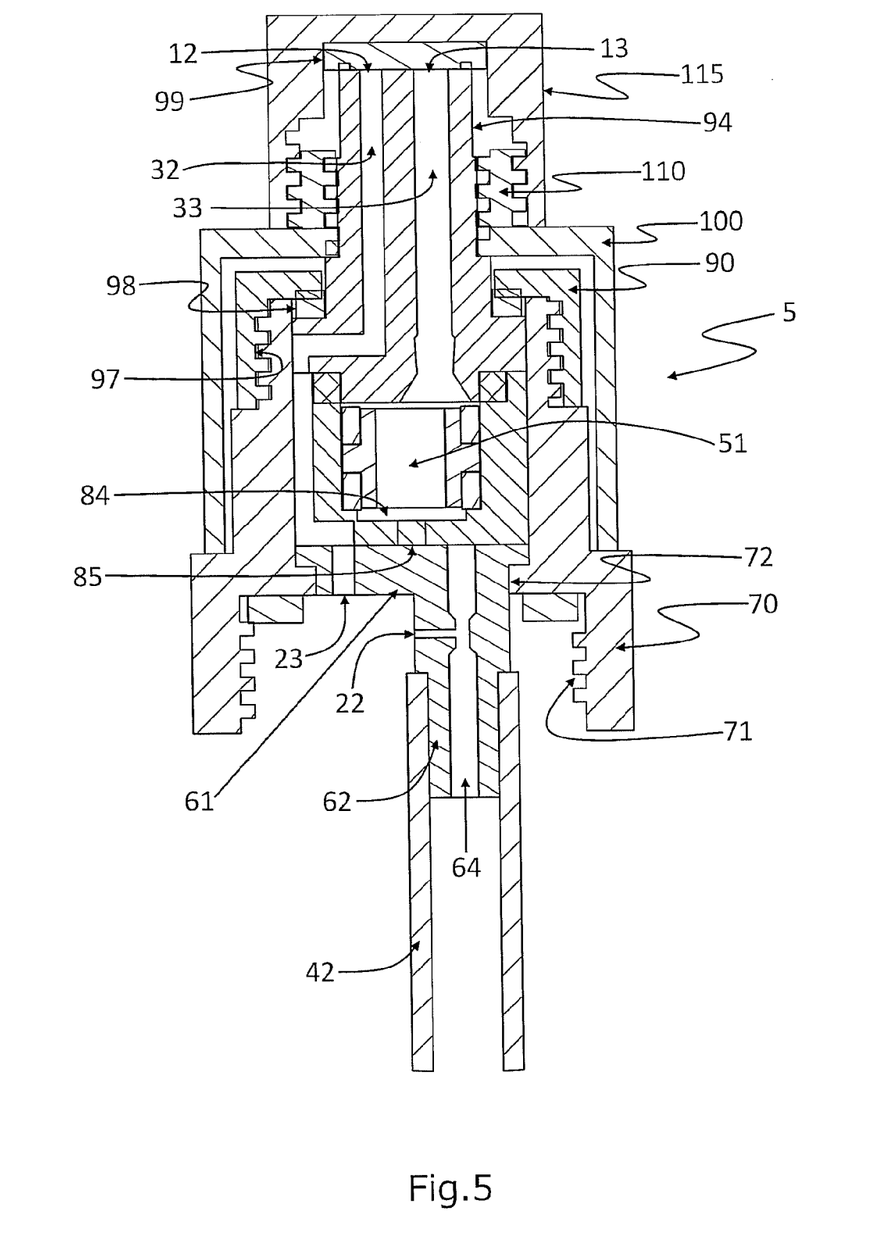
FIG. 5 is a drawing showing another aspect of the dispenser according to the present invention as a sectional view.
Figure 6:
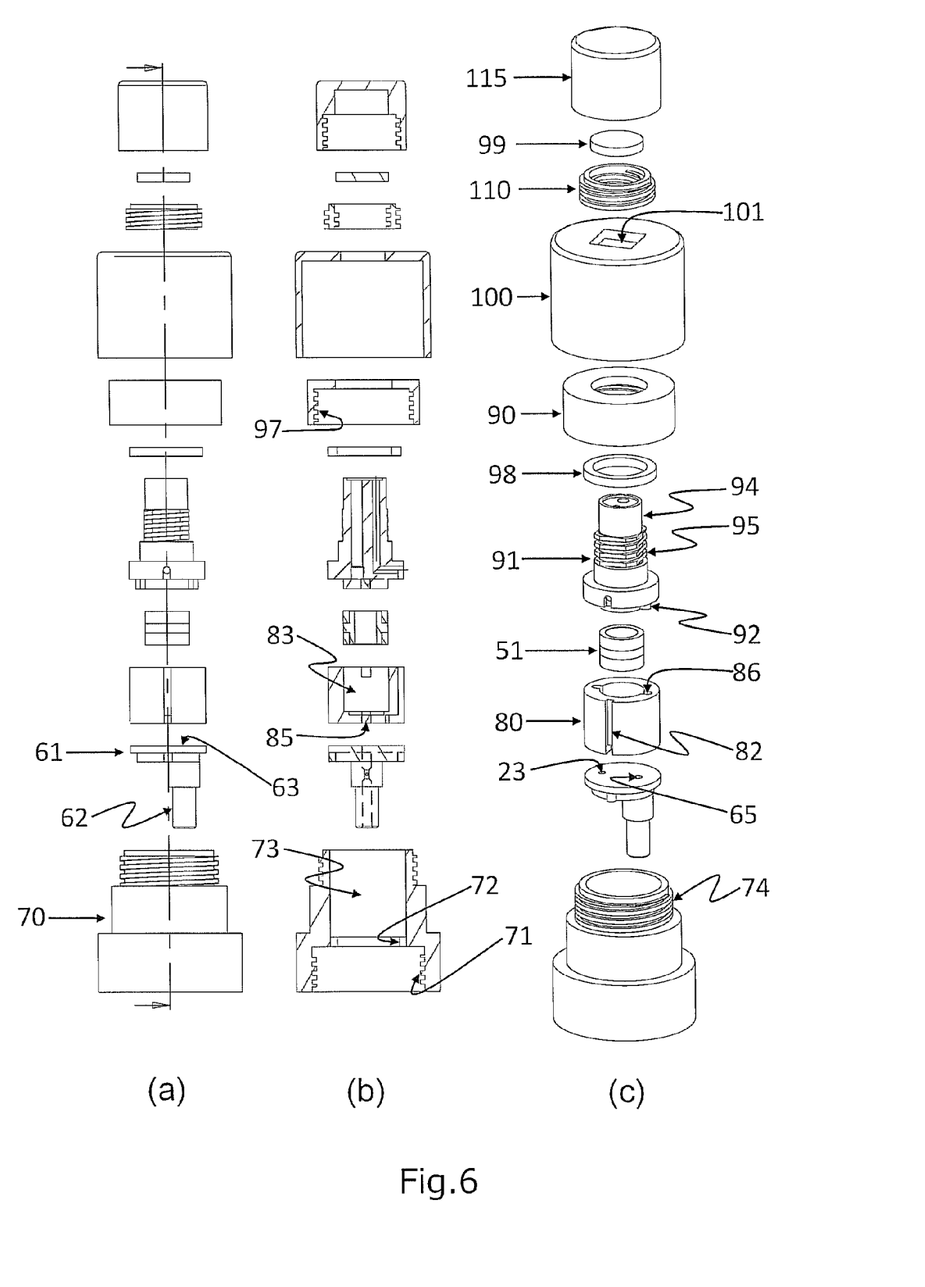
FIG. 6 includes drawings showing a disassembled state of an example of the dispenser according to the present invention and is composed of (a) a front view, (b) a sectional view, and (c) a perspective view.

Next, a structure of a dispenser capable of selectively discharging a straight forward-moving liquid or foaming liquid without attaching or detaching the caps will be described. FIG. 5 shows an example of such a dispenser. FIG. 6 includes drawings showing the arrangement of the components of the dispenser of FIG. 5 that have yet to be assembled.

Referring mainly to FIG. 6, a method for operating the dispenser of this example will be described along with the structures of the components thereof, and the like. A support member 70 serving as the main body of a dispenser 5 is shown in the lowest portion of FIG. 6. The support member 70 includes a screw 71 which is provided on the inner peripheral surface of a lower portion of the support member 70 and to be screwed into an opening of a squeeze bottle, an inner peripheral rib 72 for holding a connecting member 61 to be connected to a conduit 42 in the support member, space 73 that is provided above the rib and is intended to house a rotational member 80 for incorporating a foaming chamber 51, and an outer peripheral screw 74 to be screwed against a component holder 90 for integrating components which have been set in the support member.

The connecting member 61 connects to a conduit 42 when an insertion portion 62 thereof is inserted into the conduit 42. The rotational member 80 is slidably placed on a top pan 63 of the connecting member 61. A ventilation channel 64 for feeding air via the conduit is formed in the insertion portion 62 as penetrating through the connecting member. A second inlet 22 is formed as being perpendicular to the ventilation channel. A first inlet 23 is formed as a hole that penetrates through the top pan 63. This hole linearly parallels a groove 82 that is formed on a side surface of the rotational member 80 (as part of a first through channel). Thus, the hole constitutes part of a first channel for a straight forward-moving liquid For the rotational member 80, the foaming chamber 51 is incorporated into a hollow 83 thereof and supported by a bottom 84 thereof. Further, a hole 85 for feeding air and the content liquid to the hollow 83 is formed in the rotational member 80 as being aligned with the opening 65 of the ventilation channel 64 formed on the top pan 63 of the connecting member 61 at a predetermined position. Accordingly, when the groove 82 is aligned with the hole extending from the first inlet 23 by rotating the rotational member to a predetermined position, the first through channel opens to traffic. On the other hand, when the hole 85 and the opening 65 of the top pan are aligned, the foaming chamber 51 communicates with the conduit 42. Thus, air and the content liquid fed via the conduit and the like are introduced into the foaming chamber 51. Formed at the top end of the rotational member 80 is a notch groove 86 which is to be engaged with two ribs 92 formed in a lower portion of a valve 91. Thus, selection of the straight forward-moving liquid or foaming liquid made by the user for discharge (the direction in which the rotational member will be rotated for alignment) can be transmitted to the rotational member.

The foaming chamber 51 has a similar configuration to that of the foaming chamber 50 (see FIG. 4). After the foaming chamber 51 is installed into the hollow 83 of the rotational member 80, the valve 91 is fixed by inserting the two ribs 92 formed in the lower portion of the valve 91 into the notch groove 86 at the top end of the rotational member 80 and then pressing the valve 91 from above. At this time, the height from the bottom of the rotational member 80 to the bottom end of the valve 91 is approximately the same as the height of the foaming chamber 51. The valve 91 includes a nozzle 94. The nozzle 94 internally has a through channel 32 (part of the first through channel) through which the content liquid fed via the groove 82 passes and which connects with a first outlet 12; and a second through channel 33 through which the foaming liquid fed via the foaming chamber 51 passes and which connects with a second outlet 13.

Formed on the outer periphery of the nozzle 94 is a screw 95 for fixing the valve 91 to a switching cover 100 when a stopper 110 is screwed against the screw 95. The screw 95 has a rectangular horizontal section and can transmit a switching operation performed by the user to the valve 91 when inserted into a rectangular hole 101 formed the top surface of the switching cover 100. A section of this screw or the hole of the top surface of the switching cover need not necessarily be formed into a rectangle. Selection may be made among polygons such as a triangle and pentagon, ellipse, and the like as appropriate. Note that, as can be understood from the drawing, use of a circle or ellipse may cause a slip between the switching cover and the side surface of the valve and thus hamper switching of the valve. This point must be considered.

The valve 91 is set and then the nozzle 94 is passed through an annular gasket 98 made of silicon rubber, as well as a hole of the component holder 90. Subsequently, an inner peripheral screw 97 of the component holder 90 is screwed against an outer peripheral screw 74 of the support member 70. Thus, the rotational member, the foaming chamber, and the like are fixed. Subsequently, the switching cover 100 is fixed by the stopper 110 in a manner to operate together with the valve 91. Thus, the dispenser 5 is formed. A squeeze bottle equipped with the dispenser is kept fluid-tight by attaching a gasket 99 and a cap 115 for covering the first and second outlets.

The dispenser 5 is not a dispenser that selectively discharges a straight forward-moving liquid or foaming liquid by attaching or detaching the cap; the dispenser 5 can easily and continuously select a straight forward-moving liquid or foaming liquid by operating the switching cover. Accordingly, the dispenser 5 can be said to be superior to the above-mentioned dispenser 1 in user convenience. However, since the first and second outlets are formed in the nozzle separately, the diameter of the nozzle must be set to a large size. Accordingly, the dispenser 5 has an aspect in which in the transfer of the content liquid to another container or the like, it is difficult to aim the discharged liquid at the target. For this reason, a dispenser where an outlet of a nozzle is shared will be described below.

Figure 7:
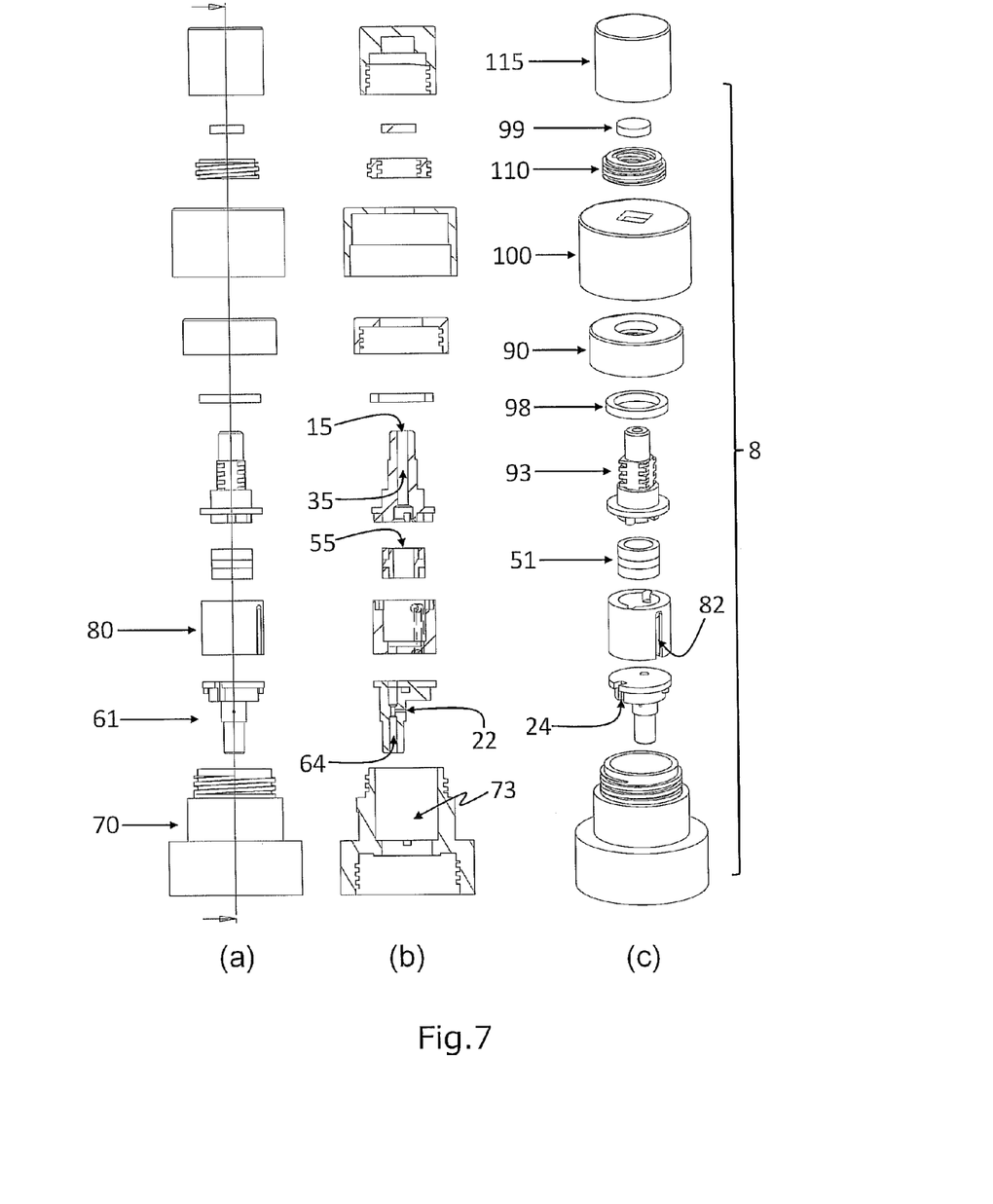
FIG. 7 includes drawings showing a disassembled state of another example of the dispenser according to the present invention and is composed of (a) a front view, (b) a sectional view, and (c) a perspective view.

FIG. 7 shows states of the yet-to-assembled components of a dispenser 8 where an outlet 15 is shared by a straight forward-moving liquid and a foaming liquid. The dispenser 8 includes similar components to those of the dispenser 5. Accordingly, portions and components having essentially the same effects and functions are given the same reference numerals and will not be described. In FIG. 7, the connecting member 61 is inserted into the space 73 of the support member 70. A channel extending from a first inlet 24 to the rotational member 80 is formed as a groove in the connecting member. While the channel is formed as a through hole in the dispenser 5, the channel may have any of those structures. The difference is that while one channel that extends straight forward toward the groove 82 on the side surface of the rotational member is formed (dispenser 8), a through hole that is temporarily given an outward course at the bottom of the rotational member and then extends straight forward toward the groove 82 is formed (dispenser 5). This difference has no special meaning.

A liquid moving straight forward through the groove 82 passes through the top surface of an exit 55 of the foaming chamber 51 in the rotational member 80 and is discharged from the outlet 15 via a through channel 35. That is, the straight forward-moving liquid passes through a first channel as follows: the straight forward-moving liquid passes through the connecting member from the first inlet 24; detours around the foaming chamber 51 in the rotational member (third through channel); and passes through the through channel 35 (second through channel). The straight forward-moving liquid is then discharged. On the other hand, a foaming liquid passes through a second channel as follows: air supplied via the conduit passes through the ventilation channel 64: the air is merged with a content liquid introduced from the second inlet 22; the air and the content liquid are sufficiently mixed in the foaming chamber 51; and the resulting foaming liquid passes through the through channel 35 (second through channel). The foaming liquid is then discharged.

The through channel 35 (second through channel) is shared by the first channel and the second channel, and the outlet 15 is shared by the straight forward-moving liquid and the foaming liquid. Accordingly, the diameter of a valve 93 of the dispenser 8 can be made smaller than that of the corresponding valve of the dispenser 5. This can make it easy to aim the discharged liquid at the target. Another advantage is that the number of through channels formed in the valve is one and therefore molding is easy. On the other hand, for the dispenser 8, for example, when a liquid which is not desired by the user (for example, a foaming liquid in the case where the user desires a straight forward moving liquid) remains on the shared channel, the undesired liquid is discharged initially. Thus, the user may be perplexed. In contrast, the dispenser 5 has an advantage that such a situation can be avoided.

While some specific examples of the present invention have been described above, the invention is not limited to the examples. For example, while part of the first channel is formed between the side surface of the rotational member 80 and the internal surface of the support member 70 in the examples of the dispensers 5 and 8, the groove 82 may be formed between the side surface of the foaming chamber 51 and the internal surface of the rotational member 80. This is effective in a case where the through channel 35 is used as a channel shared by a straight forward-moving liquid and a foaming liquid.

Further, a configuration may be employed where the entire rotational member is used as a foaming chamber; a groove for a first channel is formed on the side surface of the rotational member; and selection can be made between a straight forward-moving liquid and a foaming liquid by aligning the groove with the connecting member. In this case, the rotational member 80 serves also as a foaming chamber. Accordingly, the groove forms a first channel with the internal surface of the support member, reducing the number of components. As a result, cost can be reduced. While the connecting member and the support member are prepared as separate components, they may be molded as being integral, as a matter of course.

The dispenser 5 in FIG. 6 is configured so that switching is made between the liquids at the position where the rotational member is rotated by about 90° C. The dispenser 8 in FIG. 7 is also configured so that switching is made between the liquids at the position where the rotational member is rotated by about 90°. However, the degree of rotation may be set freely. The number of ribs of the valve used to transmit the rotation (and the corresponding notch groove of the rotational member) is not limited to two, which is shown in the example, and may be one or more. The ribs can be fixed using an adhesive or the like.

Now, a case where the dispenser 8 having the above-mentioned configuration is used, for example, in order to care contact lenses (hereafter simply referred to as lenses) will be described. Many lens care solutions contains a surfactant so as to easily remove stains attached to lenses, such as lipid. Lenses removed from the eyes are immersed in such a solution and stored. To prevent the surfaces of the lenses from being damaged during cleaning, it is preferred to foam the solution in advance and then apply the foaming solution to the lenses. On the other hand, in storing the lenses in a container, it is preferred to supply the solution in liquid form to the container.

Figure 8:
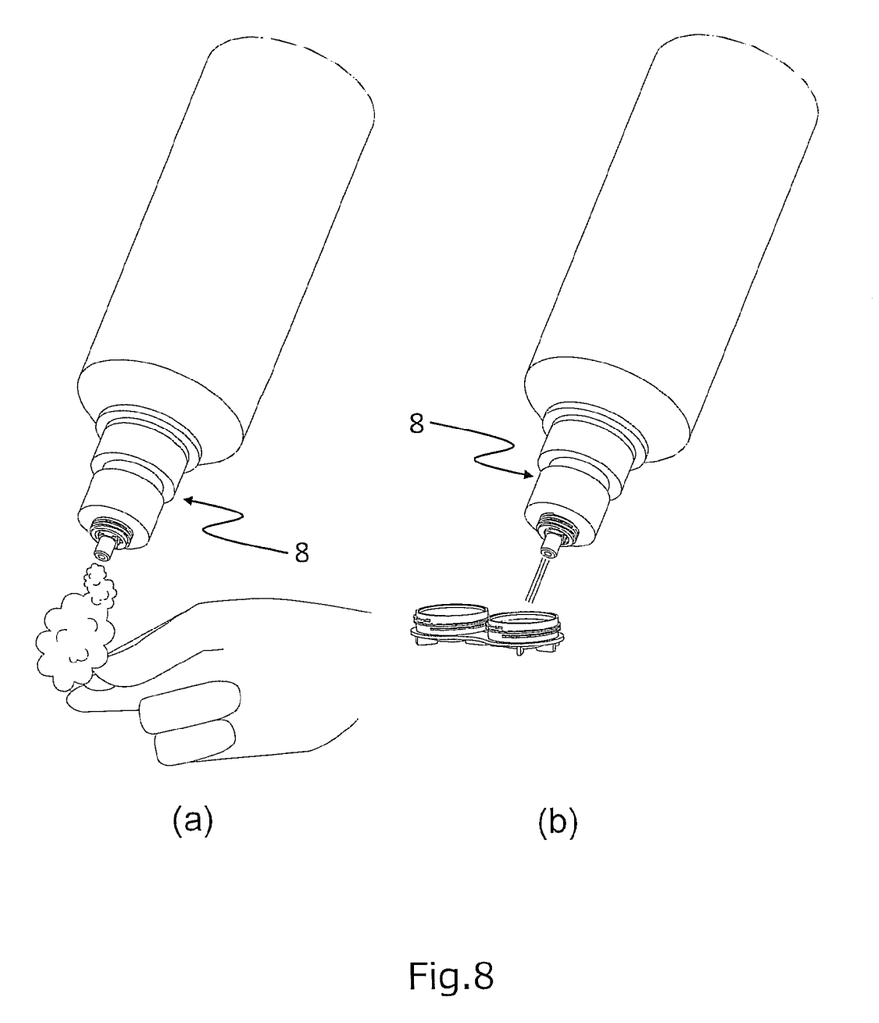
FIG. 8 is a schematic drawing showing states where an example of the dispenser according to the present invention is used for a contact lens cleaning solution and shows (a) a case where lenses are cleaned and (b) a case where the lenses are stored.

By setting the dispenser 8 to the opening of a care solution bottle as shown in FIG. 8 and operating the switching cover, a foaming liquid or straight forward-moving liquid can be selectively used in accordance with the situation, such as (a) a case where lenses are cleaned or (b) a case where the lenses are stored. Accordingly, excellent ease of use is given. Advantages of a bottle capable of discharging a foaming liquid in a different manner from traditional battles include use of a proper amount of solution onto a small object to be cleaned, such as a lens, without causing waste and with a good cleaning feeling. On the other hand, in storing the lenses, the solution can be poured into a container as has been done. There is no complicated procedure in operating the bottle. Since the solution can be used as both a foaming detergent and a soaking solution, it is possible to provide a contact lens treatment method which gives a good sense of use during cleaning and is excellent in a storage operation.

The dispenser 8 can be continuously used after the solution is exhausted, by setting it to another bottle or simply replenishing the bottle with the solution. This is economical.

The dispenser for both foam and liquid according to the present invention has a simple structure and can be operated easily. Accordingly, it can be set to the contact lens care solution container described as an example, as well as to various types of bottles, such as hand soap bottles, body wash bottles, and shampoo bottles, and used to selectively discharge a liquid in accordance with the use situation.

DESCRIPTION OF NUMERALS

1, 5, 8 dispenser
10, 12 first outlet
11, 13 second outlet
20 first inlet
21, 22 second inlet
30 first through channel
31, 33, 35 second through channel
40, 42 conduit
50, 51 foaming chamber
60 connecting pipe
70 support member
80 rotational member
91 valve
98 cap
100 switching cover
115 cap

The invention claimed is:

1. A dispenser to be attached to an opening of a squeeze bottle, the squeeze bottle being configured to discharge a content liquid when inverted, the dispenser being provided with a first channel configured to discharge a straight forward-moving liquid and a second channel configured to discharge a foaming liquid, wherein the first channel has a first through channel connecting a first inlet for the content liquid to a first outlet, the first channel having no supply channel for air, wherein the second channel has a conduit that has an opening at an inner bottom of the bottle, extends to a foaming chamber, serves as an air supply channel, and has an inner diameter of 0.8 to 4 mm; the foaming chamber connected to the conduit and configured to mix the content liquid with air to foam the content liquid; and a second through channel connecting the foaming chamber to a second outlet, and wherein a second inlet for the content liquid leading to the conduit is formed with an inner diameter size of 0.06 to 2 mm at a portion adjacent to the foaming chamber.

2. The dispenser according to claim 1,
wherein a ratio of an inner diameter of the second inlet to an inner diameter of the conduit at a position where the air and the content liquid are merged is 1/50 to 40/50.

3. The dispenser according to claim 1,
wherein the foaming chamber has a hollow tube structure where openings are formed on a side thereof adjacent to an outlet and a side thereof adjacent to an inlet,
wherein the openings are covered by screen filters, and
wherein a mesh of the filter adjacent to the inlet is set as being coarser than a mesh of the filter adjacent to the outlet.

4. A method for using the dispenser according to claim 1 to clean and store contact lenses, comprising:
cleaning contact lenses using a foaming liquid discharged from the dispenser; and
pouring a straight forward-moving liquid discharged from the dispenser into a contact lens container to store the contact lenses.

5. The dispenser according to claim 2,
wherein the foaming chamber has a hollow tube structure where openings are formed on a side thereof adjacent to an outlet and a side thereof adjacent to an inlet,
wherein the openings are covered by screen filters, and
wherein a mesh of the filter adjacent to the inlet is set as being coarser than a mesh of the filter adjacent to the outlet.

6. A method for using the dispenser according to claim 2 to clean and store contact lenses, comprising:
cleaning contact lenses using a foaming liquid discharged from the dispenser; and
pouring a straight forward-moving liquid discharged from the dispenser into a contact lens container to store the contact lenses.

7. A method for using the dispenser according to claim 3 to clean and store contact lenses, comprising:
cleaning contact lenses using a foaming liquid discharged from the dispenser; and
pouring a straight forward-moving liquid discharged from the dispenser into a contact lens container to store the contact lenses.

* * * * *